US006030846A

United States Patent [19]
Simons et al.

[11] Patent Number: 6,030,846
[45] Date of Patent: Feb. 29, 2000

[54] HOMOGENEOUS ASSAYS USING AVIDIN-BINDING AZO REAGENTS

[75] Inventors: Donald Max Simons, Wilmington; Susan Yen-Tee Tseng, Hockessin, both of Del.; Patricia Carol Weber, Kennett Square, Pa.

[73] Assignee: Dade Behring Inc., Deerfield, Ill.

[21] Appl. No.: 08/781,474

[22] Filed: Jan. 10, 1997

Related U.S. Application Data

[60] Continuation of application No. 08/453,583, May 30, 1995, abandoned, which is a division of application No. 08/264,590, Jun. 23, 1994, Pat. No. 5,536,820, which is a continuation of application No. 08/023,282, Feb. 26, 1993, abandoned.

[51] Int. Cl.[7] .................. G01N 33/53; G01N 33/536; G01N 33/543; G01N 33/542
[52] U.S. Cl. ................ 436/537; 435/7.1; 435/7.5; 435/7.92; 435/7.93; 436/536
[58] Field of Search ............. 435/7.1, 7.5, 7.92, 435/7.93; 436/536, 537

[56] References Cited

U.S. PATENT DOCUMENTS

| | | | |
|---|---|---|---|
| 4,228,237 | 10/1980 | Hevey et al. | 435/7 |
| 4,231,999 | 11/1980 | Carlsson et al. | 424/1 |
| 4,232,119 | 11/1980 | Carlsson et al. | 435/7 |
| 4,271,140 | 6/1981 | Bunting | 424/1 |
| 4,298,685 | 11/1981 | Parikh et al. | 435/7 |
| 4,659,678 | 4/1987 | Forrest et al. | 436/512 |
| 5,232,830 | 8/1993 | Van Ness | 435/6 |
| 5,332,679 | 7/1994 | Simons et al. | 436/518 |

FOREIGN PATENT DOCUMENTS

| | | | |
|---|---|---|---|
| 451810 | 4/1991 | European Pat. Off. | |
| 9216841 | 10/1992 | WIPO | G01N 33/543 |

OTHER PUBLICATIONS

Gindler, E. M. *Chemical Abstracts*, 1969, vol. 70, #44674x.
Sara, R. et al. *Chemical Abstracts*, 1991, vol. 114, #198707z.
N. M. Green, "Spectrophotometric Determination of Avidin and Biotin," Methods of Enzymol. 18A (1970) pp. 418–424.
N. M. Green, "A Spectrophotometric Assay for Avidin and Biotin Based on Binding of Dyes by Avidin," Biochem. J. (1965) 94 pp. 23c–24c.
K. J. Schray and P. G. Artz, "Determination of Avidin and Biotin by Fluorescence Polarization," Anal. Chem. 1988, 60, pp. 853–855.
D. M. Mock et al., "A Fluorometric Assay for the Biotin–Avidin Interaction Based on Displacement of the Fluorescent Probe 2–Anilinonaphthalene–6–sulfonic Acid," Analytical Biochemistry 151, pp. 178–181 (1985).
R. K. Garlick and R. W. Giese, "Avidin Binding of Radiolabeled Biotin Derivatives," The Journal of Biological Chemistry, vol. 263, No. 1, pp. 210–215.
K. Hofmann, et al., "Avidin Binding of Carboxyl–Substituted Biotin and Analogues," Biochemistry, 1982, 21, pp. 978–984.
R. M. Buckland, "Strong Signals From Streptavidin–biotin," Nature, vol. 320, Apr. 10, 1986.
Wilchek, et al., "The Avidin–Biotin Complex in Bioanalytical Applications," Analytical Biochemistry 171, 1–32 (1988).
Lichstein, et al., "Combinability of Avidin and Streptavidin with Analogs of Biotin," Biochemical and Biophysical Research Communications, vol. 20, No. 1, 1965, pp. 41–45.
J.J. L. Ho et al., "Evaluation of Factors Affecting the Performance of Enzymatic SPan–1 Immunoassays for Pancreatic Cancer," Journal of Immunological Methods, 125 (1989) pp. 92–104.
Shreve, R. N., "Studies in Azo Dyes. I. Preparation and Bacteriostatic Properties of Azo Derivatives of 2, 6–Diaminopyridine," Nov., 1943, pp. 2241–2243.
F. M. Finn, et al., "Ligands for Insulin Receptor Isolation," Biochemistry 1984, 23, pp. 2554–2558.
E. A. Bayer, et al., "3–(N–Maleimido–propionyl) Biocytin: A Versatile Thiol–Specific Biotinylating Reagent," Analytical Biochemistry 149, 529–536 (1985).
F. M. Finn, et al., "Hormone–Receptor Studies with Avidin and Biotinylinsulin–Avidin Complexes," The Journal of Biological Chemistry, vol. 255, No. 12, pp. 5742–5746 (1980).
D. E. Wolf, et al. "Amides and Amino Acid Derivatives of Biotin," J. Am. Chem. Soc., Sep. 1951, vol. 73, pp. 4142–4144.
K. Hofmann, et al., "Syntheses of Biotinylated and Dethiobiotinylated Insulins," Biochemistry 1984, 23, pp. 2547–2553.
Seaman, W., et al., "Derivatives of Phenylboric Acid, Their Preparation and Action Upon Bacteria," Feb., 1931, pp. 711–723.
Verbit, L., et al., "Benzyne Formation from Ortho–Aminophenylboronic Acid," Tetrahedron Letters No. 10, 1966, pp. 1053–1055.
Rohr, T.E., "Immunoassay Employing Surface–Enhanced Rman Spectroscopy," Analytical Biochemistry 182, 388–298 (1989).
Ikariyama, Y., "Bioaffinity Sensor With Binding Protein," (F107) pp. 693–698.
Thomas, E.W., "Resonance Raman Spectroscopic Studies of 2–(4'hydroxyphenylazo)–benzoic acid and some substituted analogs–II. Binding to Avidin and Vobine Serum Albumin," Spectrochim. Acta, vol. 35A, pp. 1251–1255.
Merlin, J.C., et al., "Resonance Raman Study of the Binding of 2–(4'Hydroxyphenlazo) Benzoic Acid on Avidin and Bovine Serum Albumin," Proceedings of the 5th International Conference on Raman Spectroscopy, Universitat Freiburt, Sep. 2–8, 1976, pp. 208–209.

(List continued on next page.)

*Primary Examiner*—James C. Housel
*Assistant Examiner*—V. Ryan
*Attorney, Agent, or Firm*—Leland K Jordan; Lois K Ruszala

[57] ABSTRACT

Avidin-binding azo reagents which alter the spectrophotometric properties of avidin and the use of such reagents in homogeneous assays are described.

3 Claims, 13 Drawing Sheets

OTHER PUBLICATIONS

Ikariyama, et al., "Sensitive Bioaffinity Sensor with Metastable Molecular Complex Receptor and Enzyme Amplifier," Anal. Chem. 1985, 57, pp. 496–500.

Ni, F, et al., "Surface–Enhanced Resonance Raman Study of Avidin–Dye Interactions: a Model for Chromophore–Containing Proteins," Journal of Raman Spectroscopy, vol. 19, pp. 429–436 (1988).

Hultin, T., "A Class of Cleavable Heterobifunctional Reagents for Thiol–Directed High–Efficiency Protein Crosslinking: Synthesis and Application to the Analysis of Protein Contact Sites in Mammalian Ribisomes," Analytical Biochemistry 155, 262–269 (1986).

Tiefenauer, et al., "Biotinyl–Estradiol Derivatives in Enzyme Immunoassays: Structural Requirements for Optical Antibody Binding," J. Sterioid Biochem., vol. 35, No. 6, pp. 633–639, (1990).

Weber, P.C., et al., "Crystallographic and Thermodynamic Comparison of Natural and Synthetic Ligands Bound to Streptavidin," J. Am. Chem. Soc., 1992, 114, 3197–3200.

Weber, P.C., et al., "Structural Origins of High–Affinity Biotin Binding to Streptavidin," Science, vol. 243, pp. 86–88, Jan. 6, 1989.

Green, N.M., "Avidin," Advances in Protein Chemistry 29: 85–133 (1975) pp. 85–133.

Norris, R. et al., "Studies in Azo Dyes. II. Preparation and Bacteriostatic Properties of Azo Derivatives of 8–Quinolinol," Nov., 1943, pp. 2243–2245.

Bayer, E.A., et al., "Affinity Cytochemistry: The Localization of Lectin and Antibody Receptors on Erthrocytes Via the Avidin–Biotin Complex," Febs Letters, vol. 68, No. 2, Oct. 1976, pp. 240–244.

Chalet, et al., "The Properties of Streptavidin, a Biotin–Binding Protein Produced by Streptomycetes," Archives of Biochemistry and Biophysics 106, 1–5 (1964), pp. 1–5.

Chignell, C.F., et al., "A Spin Label Study of Egg White Avidin," The Journal of Biological Chemistry, vol. 250, No. 14, Jul. 25, pp. 5622–5630 (1975).

Hofmann, K., et al., "iminobiotin Affinity Columns and Their Application to Retrieval of Streptavidin," Proc. Natl. Acad. Sci. USA, vol. 77, No. 8, pp. 4666–4668, Aug. 1980.

Khater, M.M., "Effect of Substitutents on the Ionization Constants of Some 8–Quinolinol Azo–Compounds," Journal f. Prakt. Chenie. Band 322, Heft 3, 1980, S– 470–474.

El–Sawi et al, Bull. Soc. Chim. Belg., vol. 94, pp. 69–73 (1985).

Gindler, Chemical Abstracts, vol. 70, #44674x (1969).

Goswami et al, Chemical Abstracts, vol. 99, #151170a (1983).

Lamble et al, Chemical Abstracts vol. 92, #216, 719p. (1980).

Majee et al, Chemical Abstracts, vol. 88, #23073g (1978).

Sara et al, Chemical Abstracts, vol. 114, #198707z (1991).

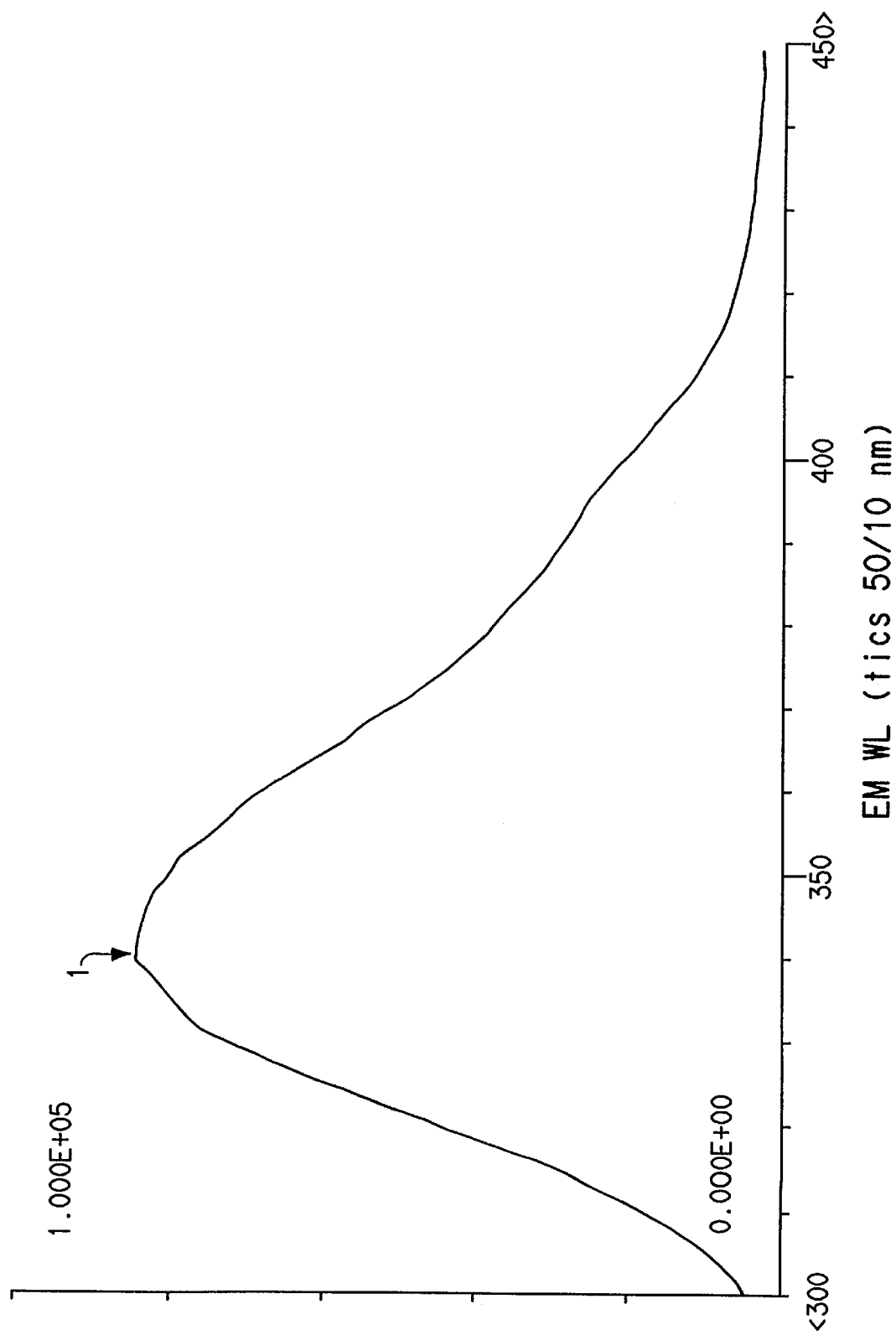

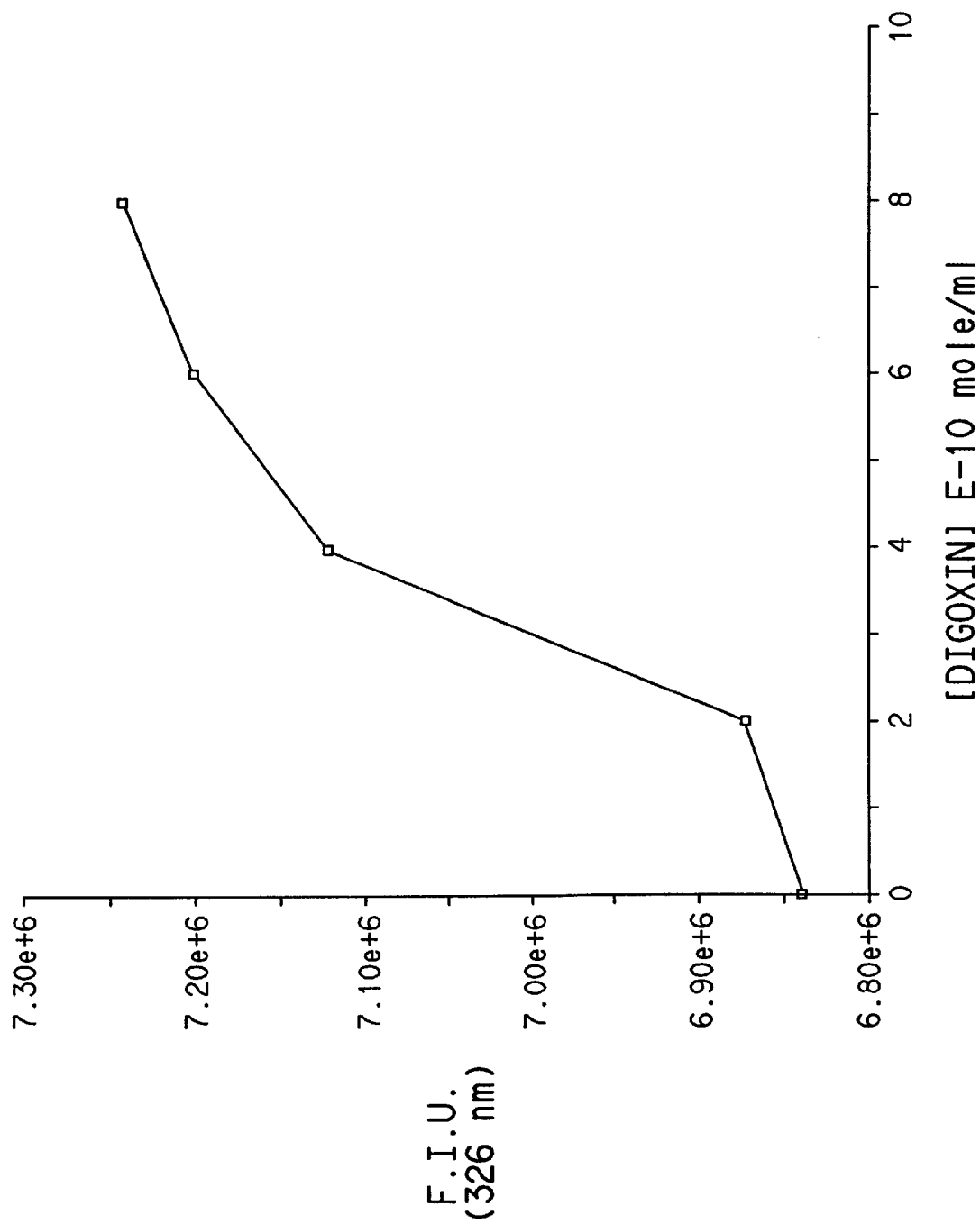

HOMOGENEOUS ASSAYS USING AVIDIN-BINDING AZO REAGENTS

This is a continuation of application Ser. No. 08/453,583, filed on May 30, 1995, abandoned, which is a division of application Ser. No. 08/264,590, filed Jun. 23, 1994 now U.S. Pat. No. 5,536,820 which is a continuation of application Ser. No. 08/023,282 filed Feb. 26, 1993, now abandoned.

FIELD OF THE INVENTION

This invention relates to homogeneous assays and, more particularly, to homogeneous assays utilizing certain avidin-binding azo reagents which alter the spectrophotometric properties of avidin as well as to these avidin-binding azo reagents.

BACKGROUND OF THE INVENTION

The strength and specificity of the avidin-biotin interaction have led to its widespread use in a variety of bioanalytical applications. The avidin-biotin complex has been used in affinity chromatography, affinity cytochemistry, cell cytometry, blotting, diagnostics, drug delivery, etc.

The biotin-avidin interaction is attractive because avidin is a small stable protein that binds four biotin molecules, and biotin is somewhat hydrophilic and easily conjugated to other molecules giving products that complex with avidin. Given the attractiveness of the biotin-avidin interaction, researchers have developed a significant number of assays utilizing biotin and avidin. These methods include microbiological, calorimetric, enzymatic, radiometric, electrochemical, and fluorescent approaches.

European Patent Application Publication No. 0 451 810 published Oct. 16, 1991 describes hapten-biotin conjugates useful in a competitive homogeneous immunoassay in which agglutination occurring during the reaction is evaluated by turbidimetric or nephelometric measurements.

U.S. Pat. No. 4,228,237, issued to Hevey et al. on Oct. 14, 1980, describes a method for determining the presence of a ligand in a liquid medium utilizing enzyme-labeled avidin and a biotinylated reagent wherein the ligand to be detected is contacted with an insoluble phase containing specific binding substance for the ligand.

Green, Biochem. J., 94: 23c–24c (1965) and Green, Methods in Enzymology, (McCormick and Wright, Eds.), Vol. 18, Part A, pages 418–424 (1970) describe the quantification of avidin by measuring changes in the optical absorbance of 4'-hydroxyazobenzene-2-carboxylic acid (HABA) upon binding to avidin; biotin can be quantitated by measuring reversal of these changes upon addition of biotin. Disadvantages of this method include relatively low sensitivity and potential interference from a variety of naturally occurring chromophores.

Mock et al., Analytical Biochemistry, 151: 178–181 (1985) describe a fluorometric assay for the biotin-avidin interaction based on displacement of the fluorescent probe 2-anilinonaphthalene-6-sulfonic acid which results in concomitant quenching of the fluorescence.

Schray et al., Anal. Chem., 60: 853–855 (1988), describe a fluorescence polarization assay utilizing a biotin-fluorescein conjugate. Polarization varies as a function of avidin concentration and, at fixed avidin levels, as a function of competing biotin concentrations. This system is quite complicated requiring multiple reagent co-optimization.

SUMMARY OF THE INVENTION

This invention relates to a composition useful in detecting the presence or absence of an analyte in a homogeneous assay, said composition comprising a complex of avidin and an azo compound, said azo compound binds in the biotin-binding site of avidin with a binding constant less than $10^{15}M^{-1}$, said azo compound having the structure:

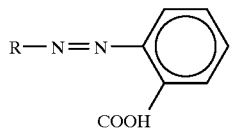

wherein R is a substituted or unsubstituted bicyclic aryl or a substituted or unsubstituted bicyclic heteroaryl.

In a second embodiment, this invention relates to a composition useful in detecting the presence or absence of an analyte in a homogenous assay, said composition comprising a conjugate of an azo compound and analyte, said conjugate binds to the biotin-binding site of avidin with a binding constant less than $10^{15}M^{-1}$ through the azo compound to form an avidin-azo compound-analyte complex, said conjugate having the structure:

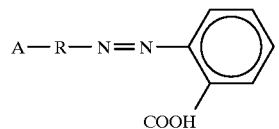

wherein

A is an analyte;

R is a substituted or unsubstituted bicyclic aryl or a substituted or unsubstituted bicyclic heteroaryl.

In a third embodiment this invention relates to a homogeneous assay to determine the presence or absence of an analyte which is a member of a specific binding pair in a sample which comprises:

a) reacting biotinylated analyte, sample suspected to contain free analyte and a constant amount of the other member of the specific binding pair;

b) reacting the product of step (a) with a constant amount of avidin-azo compound complex, said azo compound in the complex binding to the biotin-binding site of avidin with a binding constant less than $10^{15}M^{-1}$, said azo compound having the structure:

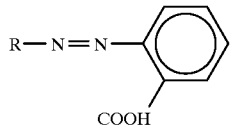

wherein R is a substituted or unsubstituted bicyclic aryl or a substituted or unsubstituted bicyclic heteroaryl;

c) measuring signal produced; and d) correlating the measurement obtained in step (c) with the amount of free analyte in the sample.

In a fourth embodiment this invention relates to a homogeneous assay to determine the presence or absence of an analyte which is a member of a specific binding pair in a sample which comprises:

a) reacting sample suspected to contain free analyte, an analyte-azo compound conjugate and a constant amount of the other member of the specific binding pair wherein the conjugate binds to the biotin-binding site of avidin with a binding constant less than $10^{15}M^{-1}$ through the azo compound, said conjugate having the structure:

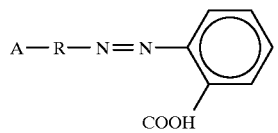

wherein

A is an analyte;

R is a substituted or unsubstituted bicyclic aryl or an unsubstituted or substituted bicyclic heteroaryl;

b) reacting the product of step (a) with a constant amount of avidin;

c) measuring signal produced; and d) correlating the measurement obtained in step (c) with the amount of free analyte in the sample.

BRIEF DESCRIPTION OF THE FIGURES

FIG. 1A depicts the fluorescence spectrum of avidin.

FIG. 11 depicts a homogeneous digoxin fluorescence immunoassay using various amounts of free digoxin (0, 2, 4, 6, and 8E-10 moles) preincubated with 6 E-10 moles (biotin)$_2$-digoxin aid 3 E-10 moles of polyclonal rabbit anti-digoxin IgG for twenty minutes at 37° C. After preincubation, avidin-NABA complex (5 E-10 moles/20 E-10 moles) was added to each sample of free digoxin and the fluorescence emission was measured.

DETAILED DESCRIPTION OF THE INVENTION

Figure 1B:
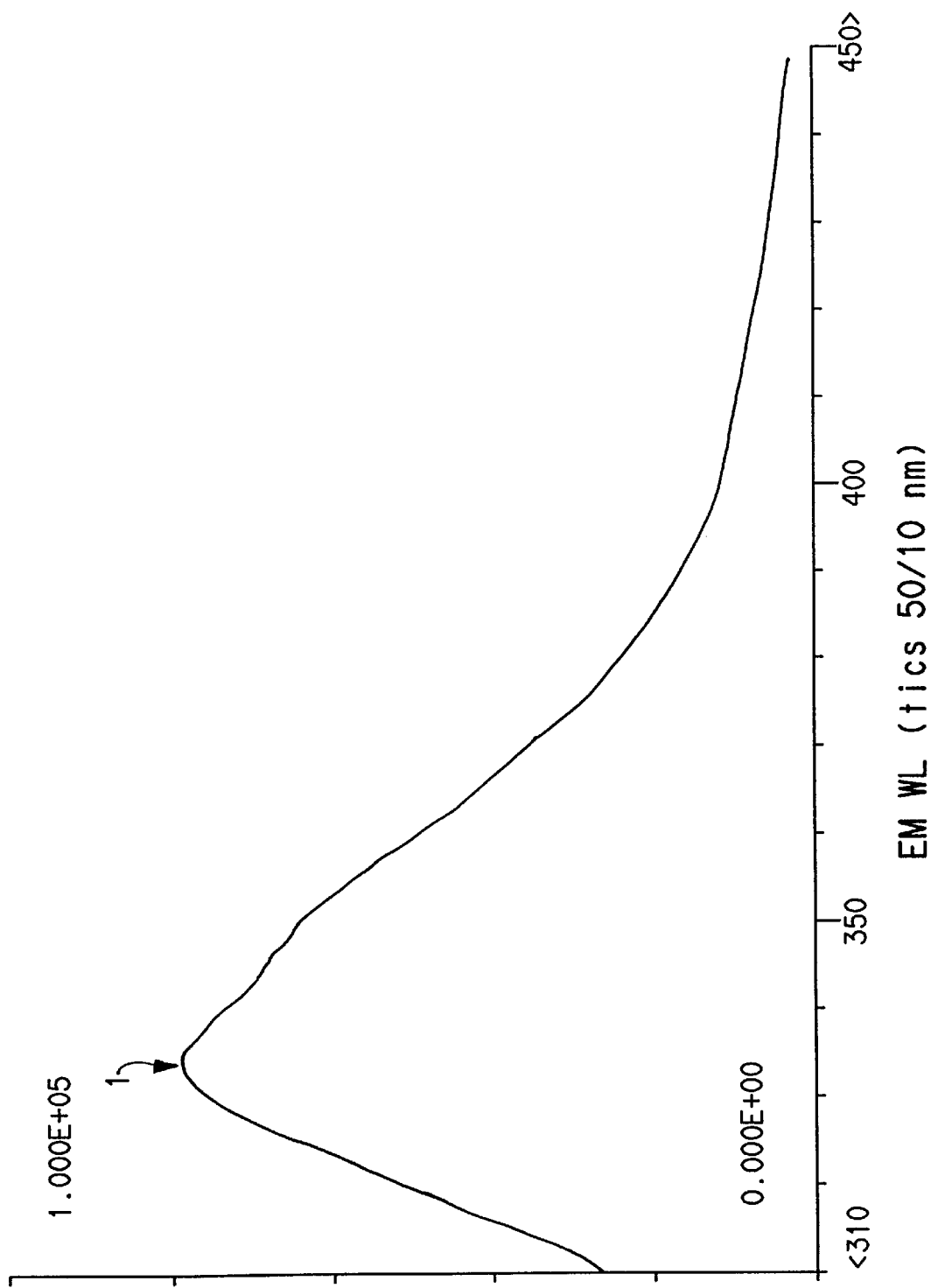
FIG. 1B depicts the fluorescence spectrum of streptavidin.

The term "avidin" as used herein means any biotin-binding compound such as avidin, streptavidin, any modified or mutant avidin produced by laboratory techniques which is capable of binding biotin or a functional equivalent of biotin, any compound designed to function like avidin, etc.

The term "biotin" as used herein means biotin, any modified biotin, and also includes biotin analogs, biotin homologs, etc.

The term "bicyclic aryl" as used herein means any bicyclic aryl compound which contains only carbon atoms in the ring system, e.g., naphthalene.

The term "bicyclic heteroaryl" as used herein means any bicyclic heteroaryl compound which contains at least one hetero atom in the ring system, i.e., an atom other than carbon such as nitrogen, oxygen, or sulfur.

It has been found that avidin-binding azo reagents can be used in homogeneous assays to facilitate detection and quantification of analytes in a simple and efficient format which heretofore has not been possible with such reagents.

Even though those skilled in the art appreciate the fact that HABA can also produce a quantifiable change in absorbance in the visible region of the spectrum as it binds to avidin, HABA cannot produce a quantifiable change in the quenching of the fluorescence of the tryptophan residues in at least one biotin-binding site of avidin and HABA cannot produce a quantifiable change in the polarization of fluorescence of tryptophan residues in at least one biotin-binding site of avidin.

In contrast, one of the unique features of the avidin-binding azo reagents of the invention and homogeneous assays using such reagents is that these reagents do produce a quantifiable change in quenching of the fluorescence of the tryptophan residues in at least one biotin-binding site of avidin and they also produce a quantifiable change in the polarization of fluorescence of tryptophan residues in at least one biotin-binding site of avidin. These quantifiable spectrophotometric changes can be measured and used in an assay to detect and/or quantify an analyte.

In one embodiment this invention concerns a composition useful in detecting the presence or absence of an analyte in a homogeneous assay, said composition comprising a complex of avidin and an azo compound, said azo compound binds in the biotin-binding site of avidin with a binding constant less than $10^{15}M^{-1}$, said azo compound having the structure prior to complexation with avidin

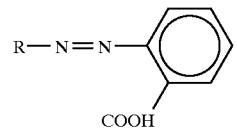

wherein R is a substituted or unsubstituted bicyclic aryl or substituted or unsubstituted bicyclic heteroaryl.

The binding constant for biotin to avidin is $10^{15}M^{-1}$. Azo compounds which can be used to practice the invention have the structures described herein and bind in the biotin-binding site of avidin with a binding constant less than $10^{15}M^{-1}$.

In addition, these azo compounds can be synthesized using conventional syntheses well known to those skilled in the art. For example, the synthesis of NABA discussed below can be modified to produce a large number of such azo compounds simply by altering the phenol component used in the synthesis. Those skilled in the art will appreciate that diazotization procedures and synthesis of azo dyes are well known and can be utilized to produce such avidin-binding azo reagents.

The azo compounds described herein produce one or more of the following spectrophotometric alterations when complexed to avidin:

(i) a quantifiable change in the absorbance of the bound azo compound in the visible region of the spectrum;

(ii) a quantifiable change in the quenching of the fluorescence of the tryptophan residues in at least one biotin-binding site of avidin; and/or (iii) a quantifiable change in the polarization of fluorescence of tryptophan residues in at least one biotin-binding site of avidin.

The bicyclic aryl or bicyclic heteroaryl moiety of the azo compound can be unsubstituted or substituted with at least one moiety such as hydroxyl. Indeed, hydroxyl is the preferred group for substituting the bicyclic aryl or bicyclic heteroaryl moiety.

Examples of such azo reagents include 2-[(4-hydroxy-1-naphthalenyl)azo]benzoic acid ("NABA"):

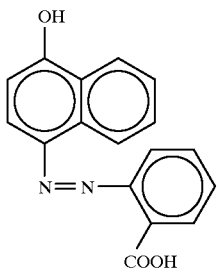

and
2-[(8-hydroxy-5-quinolinyl)azo]benzoic acid ("QABA"):

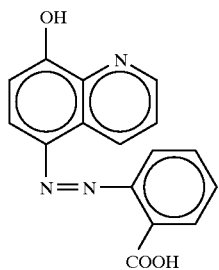

These azo compounds are complexed to avidin using conventional techniques well known to those skilled in the art. The azo compound and avidin are simply allowed to complex in solution as illustrated below.

In a second embodiment this invention concerns conjugating an analyte to an azo compound and then complexing this conjugate to avidin using standard techniques such as those discussed above. Such avidin-binding azo reagents comprise a conjugate of an azo compound and analyte wherein the conjugate binds to the biotin-binding site of avidin with a binding constant less than $10^{15}M^{-1}$ through the azo compound to form an avidin—azo compound—analyte complex, said conjugate having the structure:

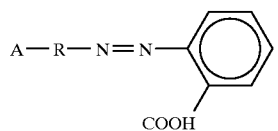

wherein
A is an analyte; and
R is a substituted or unsubstituted bicyclic aryl or a substituted or unsubstituted heteroaryl. The substitutions for R are as discussed above except that R is further substituted by conjugation to the analyte.

Conjugation of analyte to an azo compound can be effected using conventional techniques well known to those skilled in the art. Such conjugations involve two considerations: (i) the carboxylic acid group in the benzoic acid part of the molecule should remain "free", i.e., it should not be derivatized or modified because a free carboxyl moiety is important for adequate binding of the conjugate to avidin and (ii) the analyte should be conjugated to the bicyclic ring system, preferably at positions 5 or 6 as indicated below.

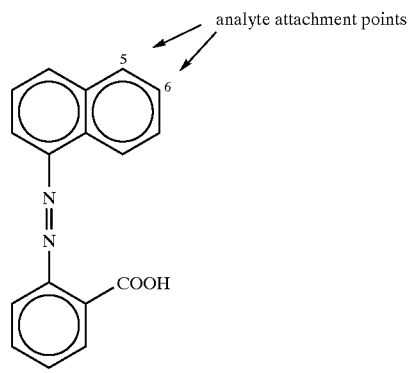

A preferred method for making conjugates entails the use of a 2-[(5-haloacetamido-4-hydroxy-1-naphthalenyl)azo] benzoic acid, since such reagents readily react with a thio-functionalized analyte, analyte derivative or analyte analog to form a stable conjugate:

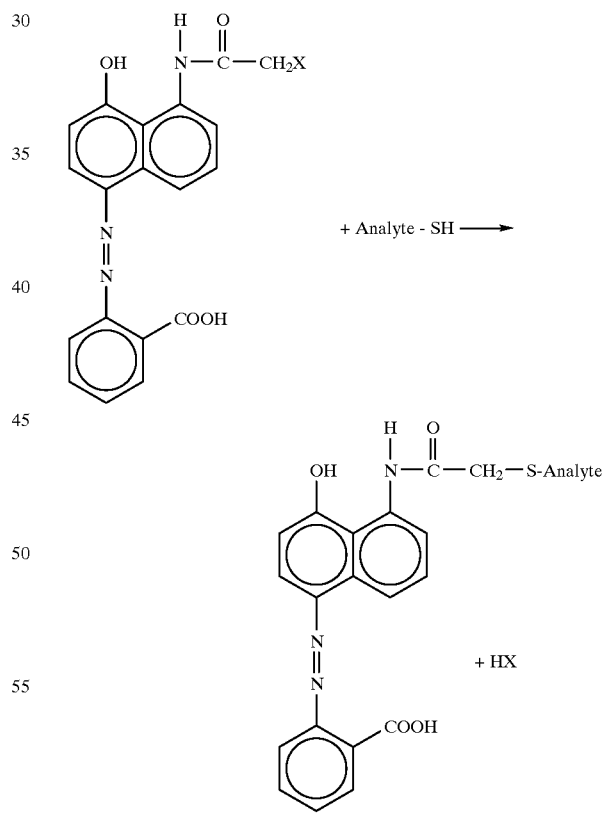

wherein X can be bromine, chlorine, iodine, p-toluenesulfonate, trifluoromethanesulfonate, etc.

Thiol functionalized analyte, analyte derivatives or analyte analogs can be readily synthesized using any number of conventional methods. For example, an amine-functionalized analyte, analyte derivative or analyte analog can be reacted with one of several commercially available reagents that introduce a free thiol, an S-thiol ester which is hydrolyzable to free thiol or a disulfide group which can be reduced to a free thiol. Examples of such reagents include DL-N-acetylhomocysteine thiolactone, S-acetylmercaptosuccinic anhydride, disuccinimidyl 3,3'-dithiodipropionate, DL-homocysteine thiolactone hydrochloride, 2-iminothiolane hydrochloride, pentafluorophenyl S-acetylthioacetate, 3(2-pyridyldithio)propionic acid, succinimidyl S-acetylthioacetate, succinimidyl 3-(acetylthio)propionate, succinimidyl 3-(2-pyridyldithio) butyrate, succinimidyl 4-(1-(2-pyridyldithio)ethyl)benzoate, succinimidyl 3-(2-pyridyldithio)propionate, etc.

An hydroxyl-functionalized analyte, analyte derivative or analyte analog can be converted to the corresponding p-toluenesulfonate ester, trifluoromethanesulfonate ester, bromide, or iodide, and then reacted with thioacetic acid to introduce an acetyl-protected thiol. The acetyl protecting group can be removed by hydrolysis, or preferably with hydroxylamine. Reaction of thioacetic acid with bromides and tosylates is exemplified in the following references, the disclosures of which are hereby incorporated by reference: W. A. Bonner. The acid-catalyzed anomerization of the D-glucose pentaacetates. A kinetic thermodynamic and mechanistic study. *J. Am. Chem. Soc.* 73: 2659–2666 (1951); D. R. Strobach. The reaction of potassium thiolacetate with $2^1$,5-di-O-polylsulfonyl-α-D-isosaccharin. *Carbohyd. Res.* 17: 457–460 (1971).

An analyte, analyte derivative or analyte analog containing a double bond can be reacted with thioacetic acid to introduce an acetyl-protected thiol. The acetyl protecting group can be removed by hydrolysis, or preferrably with hydroxylamine. Reaction of thioacetic acid with double bonds is exemplified in the following references, the disclosures of which are hereby incorporated by reference: R. M. Dodson and R. C. Tweit. Addition of alkanethiolic acids to $D^{1,4}$-3-oxo and $D^{4,6}$-3-oxosteroids. *J. Am. Chem. Soc.* 81: 1224–1227 (1959);. E. Walton, A. F. Wagner, F. W. Bachelor, L. H. Peterson, F. W. Holly and K. Folkers. Synthesis of (+)-α-lipoic acid and its optical antipodes. *J. Am. Chem. Soc.* 77: 5144–5149 (1955).

Any analyte which is a member of a specific binding pair can be determined using the compositions and homogeneous assay of the invention. Specific binding pairs can be immune or non-immune.

Immune specific binding pairs are exemplified by antigen/antibody systems or hapten/anti-hapten systems. If an antibody is used, it can be polyclonal, monoclonal, or an immunoreactive fragment thereof. Such antibodies and fragments can be produced by customary methods familiar to those skilled in the art.

The terms "immunoreactive antibody fragment" or "immunoreactive fragment" mean fragments which contain the binding region of the antibody. Such fragments may be Fab-type fragments which are defined as fragments devoid of the Fc portion, e.g., Fab, Fab', and F(ab')$_2$ fragments, or may be so-called "half-molecule" fragments obtained by reductive cleavage of the disulfide bonds connecting the heavy chain components of the intact antibody or single chain antibodies produced by recombinant DNA methods.

Non-immune binding pairs include systems wherein the two components share a natural affinity for each other but are not antibodies. Exemplary non-immune binding pairs include folic acid-folate binding protein, complementary probe nucleic acids, etc.

The homogeneous assay of the invention can be used to determine the presence or absence of an analyte which is a member of a specific binding pair in a sample which comprises:

a) reacting biotinylated analyte, sample suspected to contain free analyte and a constant amount of the other member of the specific binding pair;

b) reacting the product of step (a) with a constant amount of avidin-azo compound complex, said azo compound in the complex binding to the biotin-binding site of avidin with a binding constant less than $10^{15}M^{-1}$, said azo compound having the structure:

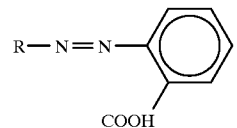

wherein R is a substituted or unsubstituted bicyclic aryl or a substituted or unsubstituted bicyclic heteroaryl;

c) measuring signal produced; and d) correlating the measurement obtained in step (c) with the amount of free analyte in the sample.

A wide variety of techniques are available for synthesizing biotin-analyte conjugates useful in practicing the method of this invention.

For example analytes, analyte derivatives or analyte analogs that are functionalized with a carboxylic acid group can be converted to the corresponding isourea esters or succinimidyl esters and then reacted with biotin hydrazide, biocytin hydrazide, or 6-((biotinoyl)amino)caproic acid hydrazide.

In another approach, analytes, analyte derivatives or analyte analogs that are functionalized with a carboxylic acid group can be converted to the corresponding isourea esters or succinimidyl esters and then reacted with N-(2-aminoethyl)biotinamide, N-(5-aminopentyl)biotinamide, 2-(((N-(biotinoyl)amino)hexanoyl)amino)ethylamine, 5-(((N(biotinoyl)amino)hexanoyl)amino)pentylamine, or biocytin.

Analytes, analyte derivatives or analyte analogs that are functionalized with an amine group can be reacted directly with succinimidyl D-biotin, succinimidyl 6-(biotinamido) hexanoate, or succinimidyl 6-((6-((biotinoyl)amino) hexanoyl)amino)hexanoate.

Analytes, analyte derivatives or analyte analogs that are functionalized with a thiol group can be reacted with 3-(N-maleimidylpropionyl)biocytin, N-biotinoyl)-N'-(iodoacetyl) ethylenediamine, or biocytin iodoacetamide.

Analytes, analyte derivatives or analyte analogs that contain a phenolic ring with an unblocked ortho- or para-position can by coupled to diazotized p-aminobenzoyl biocytin.

In the first assay format discussed above, fluorescence increases as the azo compound is displaced from avidin and there is a concomitant decrease in polarization.

In a second embodiment, this assay can be performed by:

a) reacting sample suspected to contain free analyte, an analyte-azo compound conjugate and a constant amount of the other member of the specific binding pair wherein the conjugate binds to the biotin-binding site of avidin with a binding constant less than $10^{15}M^{-1}$ through the azo compound, said conjugate having the structure:

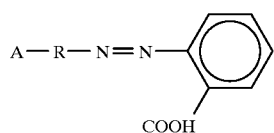

wherein

A is an analyte;

R is a substituted or unsubstituted bicyclic aryl or an unsubstituted or substituted bicyclic heteroaryl;

b) reacting the product of step (a) with a constant amount of avidin;

c) measuring signal produced; and d) correlating the measurement obtained in step (c) with the amount of free analyte in the sample.

In the second format, fluorescence decreases as the analyte-azo compound conjugate binds to avidin and there is also a concomitant increase in polarization.

The following example(s) illustrate practice of the invention but should not be construed as a limitation thereon.

EXAMPLE 1

Determination of Digoxin Concentration in a Competitive Homogeneous Fluorescence Assay Utilizing the Avidin-Binding Azo Reagent, Avidin-NABA A. Reagents 1. Synthesis of NABA This synthesis can be used to make almost any of the azo compounds which can be used to practice the invention simply by substituting different phenols into the experimental protocol.

a) Reagents

Anthranilic acid—FW=137.14

Conc. HCL—FW=36.46; density 1.18–1.19; % % HCl 36.5–38; normality 12.

Sodium nitrite—FW=69.00

Sulfamic acid—FW=97.09; 10% aqueous solution

Starch-iodide test paper

1-Naphthol=FW 144.17

Sodium hydroxide—FW=40.00

Acetic Acid—Recrystallization solvent b) Procedure

1. Firmly clamp a 250-mL beaker to a vertical support rod in a hood. Adjust the height of the beaker to about 12 inches above the floor of the hood. Equip the beaker with a thermometer and a mechanical stirrer. Add a solution of 19.0 mL of conc. HCl in 50 ml of water to the beaker. Place a dry ice-acetone bath on a Labjack under the beaker and raise the jack until the bath liquid contacts the bottom of the beaker. Allow the acid solution to cool to about 0° C. Sift in 6.50 grams of finely divided anthranilic acid (no lumps!) while stirring the solution mechanically. (The anthranilic acid does not dissolve completely.)

2. Add an ice-cold solution of 3.60 grams sodium nitrite in 20 mL of water portionwise to the anthranilic acid suspension while stirring and maintaining the temperature as −5–0° C. The anthranilic acid dissolves as the diazotization proceeds. Stir the solution for about 15 minutes after addition of the nitrite solution is complete.

3. Keep the temperature at −5–0° and destroy the excess nitrous acid by alternately adding a few drops of cold 10% sulfamic acid solution and then testing for the presence of nitrous acid with starch—iodide paper. Caution: The solution foams due to liberation of nitrogen. When a drop of the reaction mixture placed on starch—iodide paper no longer gives an immediate blue color, the nitrous acid has been destroyed.

4. Set up a 400 mL beaker as described in Step 1 above. Place 16.0 grams of sodium hydroxide pellets in the beaker and add 175 mL of water. Stir the mixture mechanically. When the sodium hydroxide has dissolved, add 7.21 grams of 1-naphthol. Heat the solution until the phenol dissolves, then cool the mixture with a dry ice—acetone bath to about 0°. (The phenol may reprecipitate.) Add the diazotized anthranilic acid from Step 4 to the alkaline phenol while stirring vigorously and holding the temperature at 0–5°. The mixture immediately turns deep red. After the addition is complete, replace the dry ice bath with an ice bath and continue stirring the reaction mixture for about 45 minutes.

5. Acidify the reaction mixture with 50 mL of 1:1 conc. HCl/water. The product precipitates during this operation. Allow the mixture to stand overnight at room temperature.

6. Filter the product with suction and allow to air-dry. Wt. of crude product, 13 grams (90%).

7. Recrystallization: Most azo dyes can be crystallized from ethanol or ethanol/water. However NABA was not very soluble in hot ethanol so glacial acetic acid was used instead.

2. Synthesis of (Biotin)$_2$-digoxin conjugate

The biotin-digoxin conjugates used herein can be synthesized by methods well-known in the art. For example, a conjugate containing two biotin molecules per digoxin molecule was prepared by oxidizing digoxin to the dialdehyde— as described by D. R. Hwang, M. E. Scott and E. Hedaya (*Bioconjugate Chem.* 1: 309–313 [1990]), the disclosure of which is hereby incorporated by reference, and treating the digoxin dialdehyde so made with biotin hydrazide (2 moles of hydrazide per mole of dialdehyde.

Specifically, the (biotin)$_2$-digoxin conjugate was synthesized as follows:

1. Set up a one-neck, round-bottomed 100-mL flask, provided with an nitrogen inlet and magnetic stirrer. Flush the system with nitrogen, and maintain a nitrogen atmosphere during the reaction.

2. Place 1000 mg (1.280 mmoles) of digoxin in the flask. Add 20 mL of chloroform/methanol (2:1). Stir the mixture until the solid has dissolved.

3. Stir the digoxin solution vigorous and add a solution of sodium periodate (625 mg; 2.922 mmoles) in 5 mL of water. Stir the mixture vigorously for 30 minutes.

4. Transfer the reaction flask to the rotary evaporator and remove solvent until a pasty mass remains. (It is not necessary to remove all of the residual water.) Add 60 mL of chloroform and 6 mL of water to the residue. Transfer the mixture to a separatory funnel. Draw off the chloroform (bottom) layer and extract the aqueous layer with three 20-mL portions of fresh chloroform. Combine the chloroform extracts with the original.

5. Dry the combined chloroform extracts over anhydrous magnesium sulfate. Filter to remove the drying agent and remove the chloroform in a rotary evaporator. Dissolve the residue in 15 mL of glacial acetic acid.

6. Add 661 mg of biotin hydrazide in 5 mL of warm glacial acetic acid. Stir the solution overnight at room temperature.

7. Remove as much of the acetic acid as possible on the rotary evaporator. Triturate the residue with 20 mL of ether. Transfer the suspension to a polypropylene centrifuge tube.

8. Centrifuge the suspension and wash the residue twice with 5-mL portions of ether. Air-dry the product for about an, hour, then complete the drying in a vacuum desiccator. Wt. of crude product, 1.46 grams.

9. Suspend the crude product in 35 mL of 0.15 M sodium bicarbonate and add 256 mg of powdered succinic anhydride portionwise over the course of 15 minutes. Continue the stirring for about 15 minutes after the addition is complete. During the entire operation add small quantities of solid sodium bicarbonate as necessary in order to maintain the pH at about 8. (The purpose of this step is to remove unreacted biotin hydrazide).

10. Centrifuge the suspension. Discard the supernatant liquid and wash the residue three times with 5-mL portions of water. Dry the residue thoroughly in a vacuum desiccator. Recovery, 917 mg.

11. Dissolve the residue in 6 mL of methanol. Add the methanol solution dropwise to 25 mL of dry ether with vigorous stirring to precipitate the product. Centrifuge the mixture and discard the supernatant liquid. Wash the residue three times with 10-mL portions of ether. Dry the product thoroughly in a vacuum desiccator. Recovery, 500 mg.

Alternatively, a biotin-digoxin conjugate containing one biotin and one digoxin residue was prepared by reaction of digoxigenin-3-O-methylcarbonylaminocaproic acid-N-hydroxysuccinimide ester (available from Boehringer Mannheim Corporation) with biotin hydrazide in a 1/1 mole ratio.

B. Spectroscopic Properties of Avidins, Azo Dyes, and Avidin-Azo Dye Complexes

1. Avidin

Affinity-purified egg white avidin and culture filtrates of Streptomyces species were purchased from Pierce Chemical Co. Avidin and streptavidin concentration were assessed by the absorbance at 282 nm [$E_{subunit}$=24 mM$^{-1}$ cm$^{-1}$, $E_{1\%}$=15.4 cm$^{-1}$] and [$E_{subunit}$=34 mM$^{-1}$ cm$^{-1}$, $E_{1\%}$=22.5 cm$^{-1}$] respectively (N. M. Green, Advance in protein chemistry 29: 85–133 (1975)).

1a) Ultraviolet Absorbance:

The absorption spectrum of avidin and streptavidin are directly involved of aromatic amino acid residues in the biotin binding site (Green, 1962). Each subunit of avidin contains four tryptophan residues in the binding site and streptavidin has two additional tryptophan residues located outside the binding site. Consequently, it is preferred to use avidin which does not have additional tryptophan residues outside of the binding site.

1b) Fluorescence Spectrum:

The aromatic amino acid residues of tryptophan in the avidin or streptavidin are the main contributors of fluorescence emission spectrum. The fluorescence spectra of avidin and streptavidin is shown in FIGS. 1A and 1B.

Figure 5:
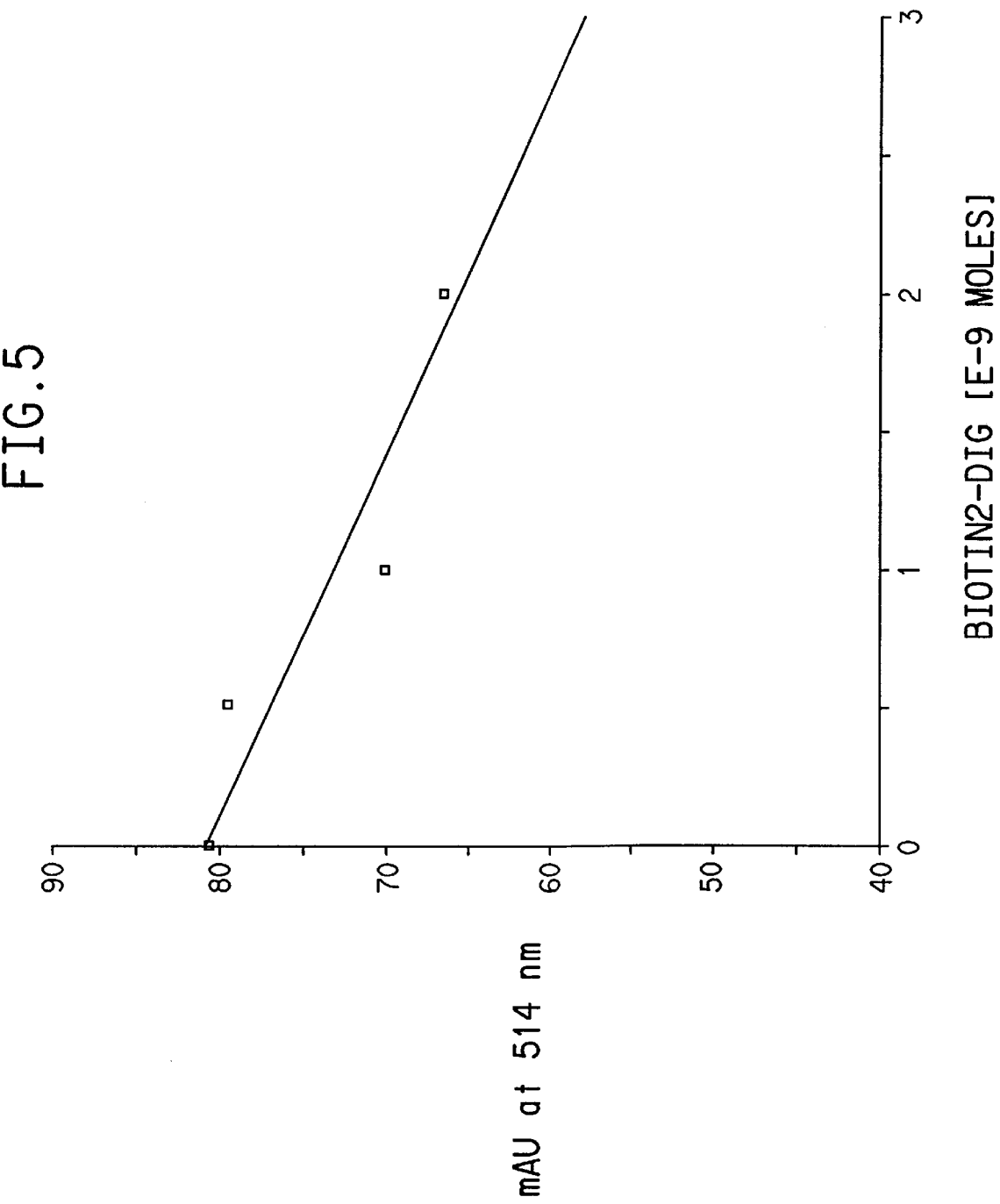
FIG. 5 depicts results of a calorimetric assay for (biotin)$_2$-digoxin to displace NABA from a NABA-avidin complex.

In FIG. 1A, 5.58E-10 moles of egg white avidin fluorescence emission spectrum was measured on an AMINCO Photon Counter 8000C. The parameters were as follows: excitation wavelength was 300 nm, emission wavelength was at 342 nm, scanning from 300 to 450 nm, EX/EM band width:16/16 nm, signal integration time: one second.

In FIG. 1B, 5.0 E-10 moles of streptavidin fluorescence spectrum was measured on an AMINCO Photon Counter 8000C. The parameters were as follows: excitation wavelength at 310 nm, emission wavelength at 342 nm, scanning from 310 to 450 nm, EX/EM resolution band width: 8/8 nm, signal integration time: one second.

2. Azo Dye—NABA

2a) Ultraviolet and visible spectrum

Figure 2:
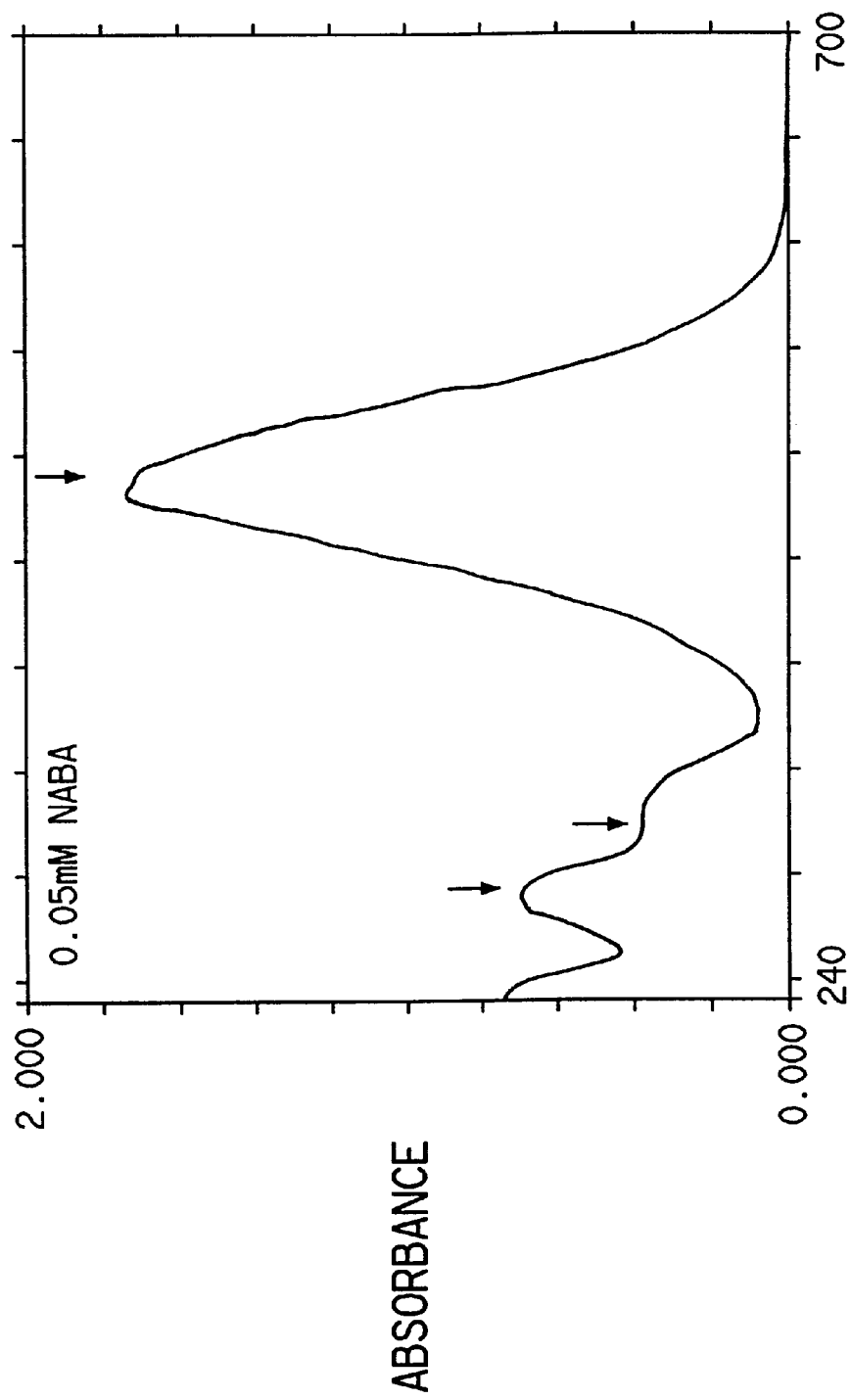
FIG. 2 depicts the ultraviolet-visible scan of NABA on an HP8452A spectrophotometer from 240–700 nm. Maximum absorption of NABA was at 488 nm.

NABA produces a bright orange color. One ml of 0.05 mM aqueous NABA solution had a maximum absorption band at 488 nm wavelength as measured on an HP8452A spectrophotometer over the region from 240 to 700 nm. This is shown in FIG. 2. The extinction coefficient at 488 nm for NABA was $3.13 \times 10^4$ M$^{-1}$ cm$^{-1}$.

2b) Fluorescence spectrum

Figure 3:
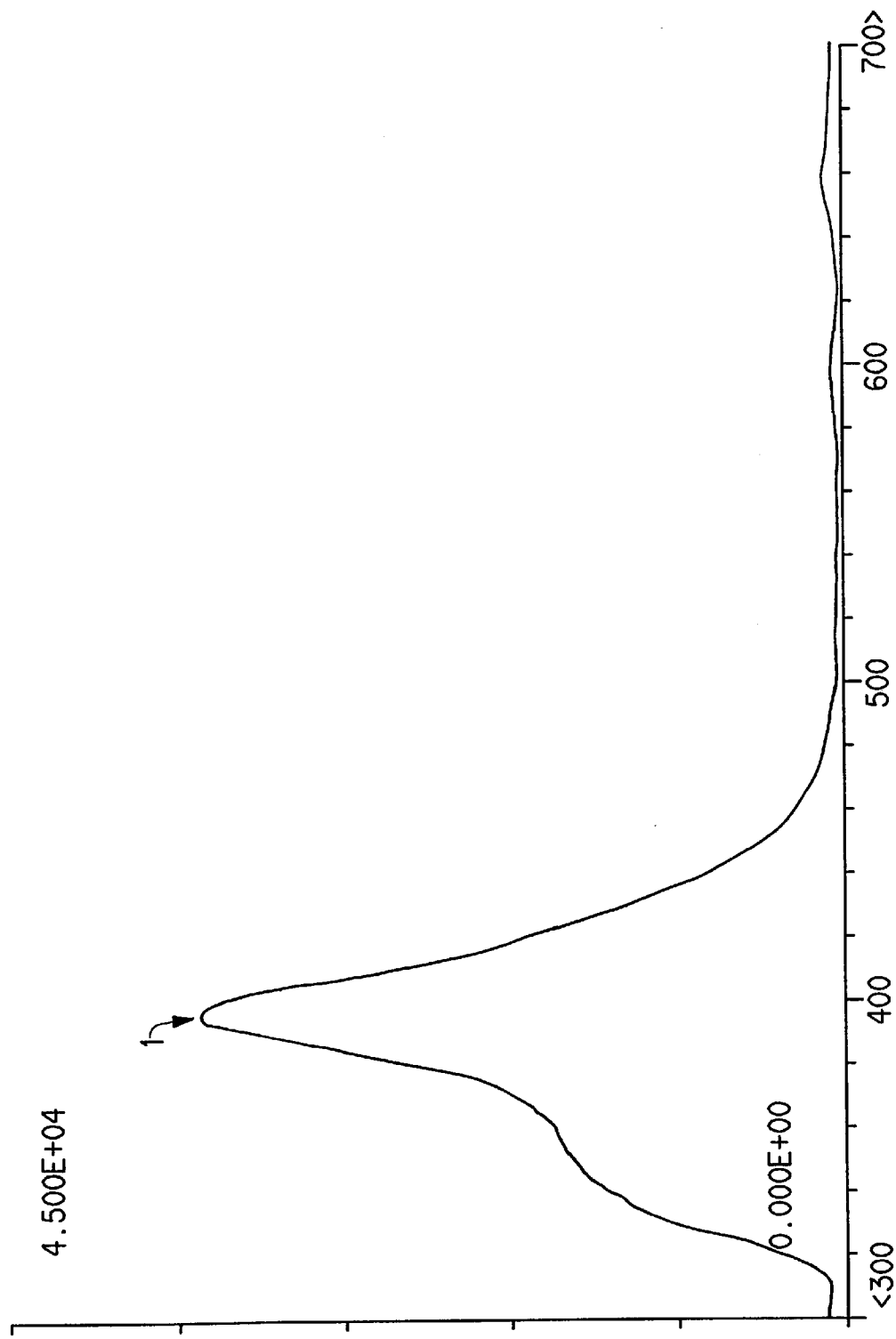
FIG. 3 depicts the fluorescence emission spectrum of NABA.

The fluorescence emission spectrum of NABA shows the maximum wavelength at 398 nm. The fluorescence emission of one ml of 0.05 mM NABA was recorded on an AMINCO Photon Counter 8000C. The parameters were as follows: excitation wavelength at 300 nm, emission wavelength at 398 nm, scanning from 300 to 700 nm; EX/EM resolution band width: 16/16 nm; signal integration time: one second. The fluorescence spectrum of NABA is presented in FIG. 3.

3. Avidin or Streptavidin—Azo Dye Complexes

Figure 4A:
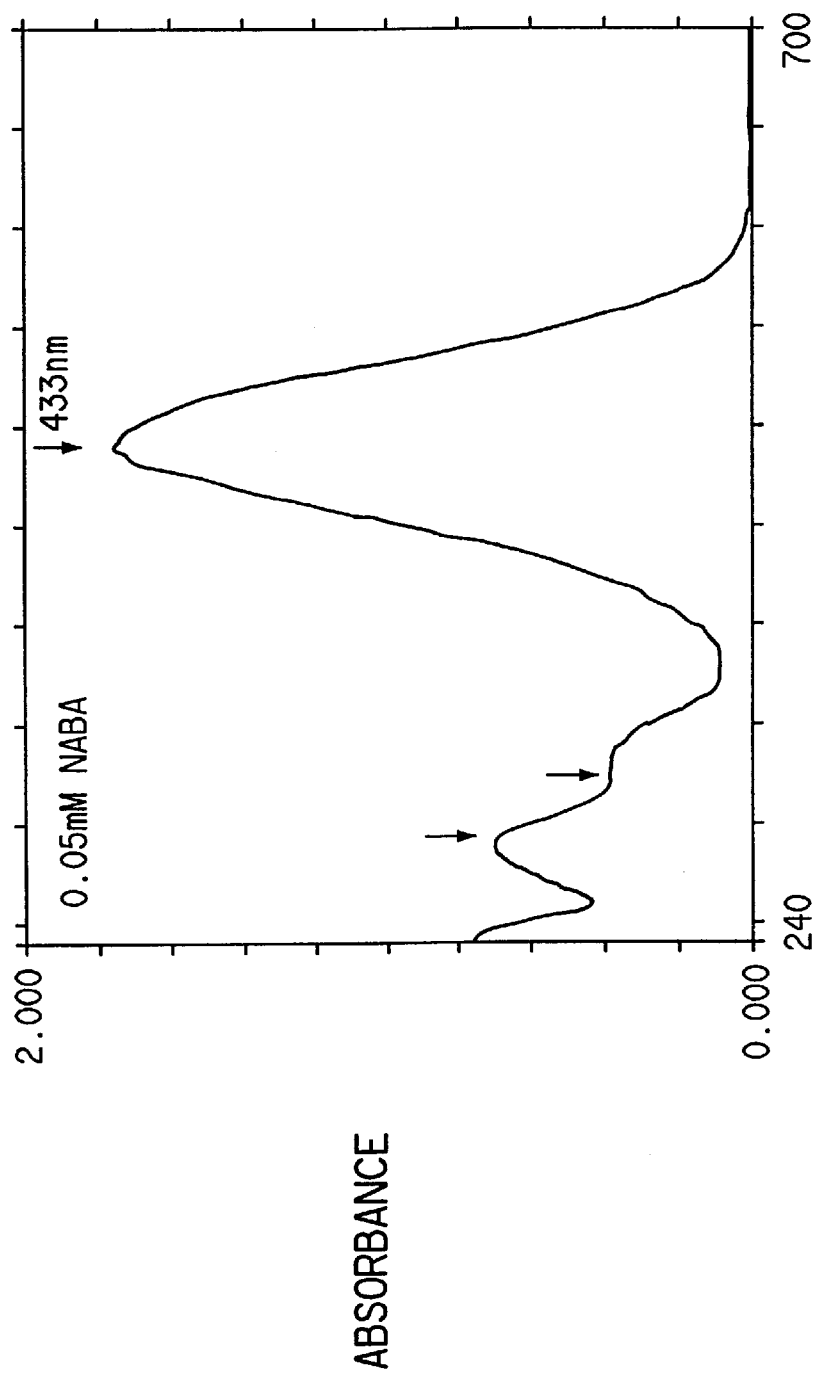
FIG. 4 depicts the ultraviolet-visible spectrum of an avidin-NABA complex.
Figure 4B:
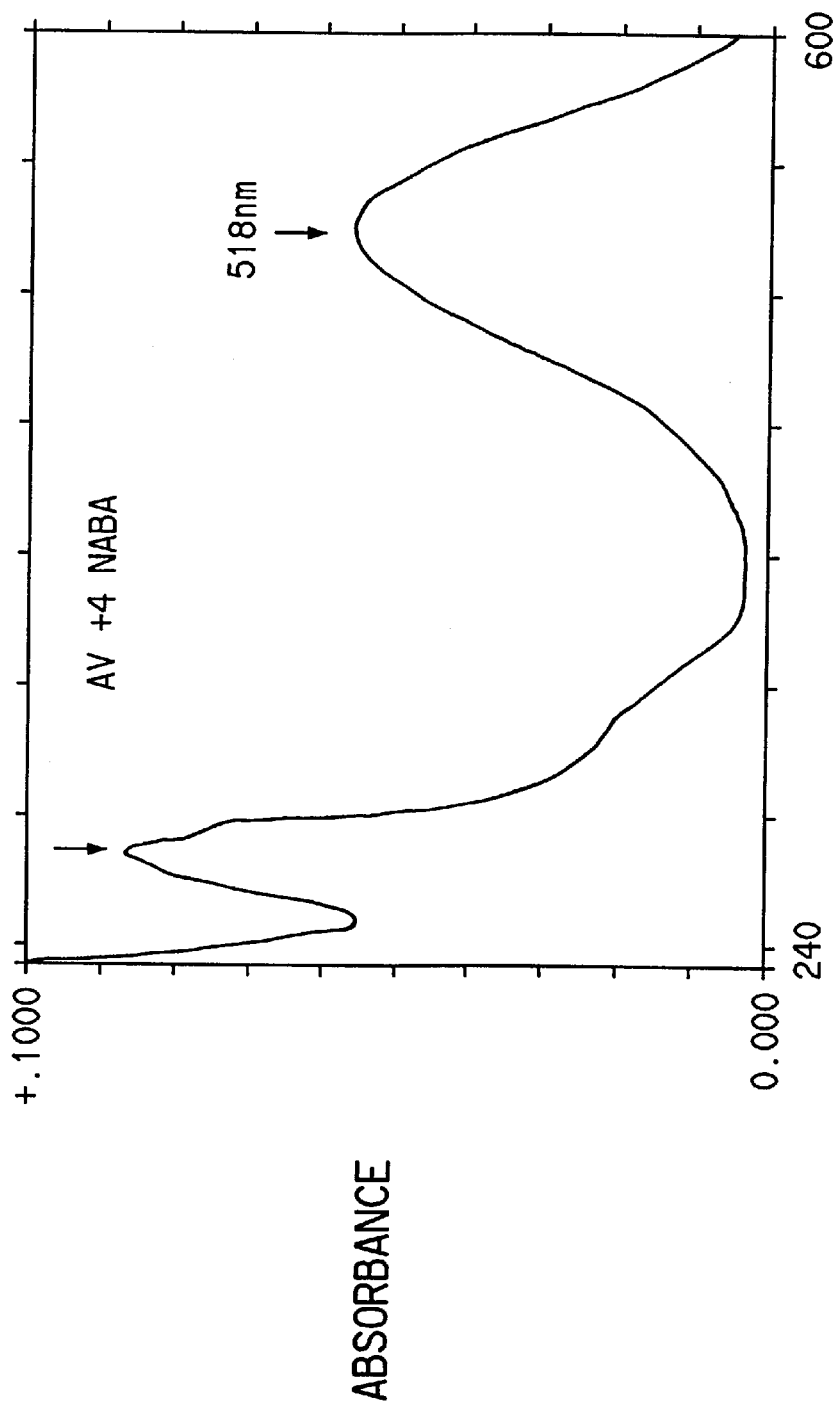

3a) Colorimetric spectrum shift:

The binding of an azo dye to avidin is accompanied by a red spectrum shift (from 488 nm to 518 nm) for the azo compound. The UV-Vis spectrum of an avidin-NABA complex is shown in FIG. 4. The UV-Vis scans of NABA and NABA-avidin were measured on an HP8452A spectrophotometer over the range 240 to 600 nm. The maximum absorption wavelength of the azo compound, NABA, shifted from 488 to 518 when complexed to avidin.

Colorimetric assay for biotin or biotinylated conjugates 1 ml of avidin-NABA complex solution ($5 \times 10^{-10}/20 \times 10^{-10}$ mole/ml of AV/NABA in 0.1 M sodium bicarbonate buffer at pH 8.5) was pipetted into a 1-cm cuvette. The absorption of the complex was measured in a spectrophotometer (HP 8452A). 10 to 40 $\mu$l of $5 \times 10^{-11}$ mole/ml of biotin (Sigma Chemical Co.) was added to the complex and the absorption of each was measured in a spectrophotometer. The concentration of biotin was plotted against the absorption ratio at 514 nm of the mixtures. The same assay can be used to determine the biotin—analyte conjugate concentration in the sample. Biotinylated conjugates such as biotin-digoxin, displaced NABA from the avidin-NABA complex and the concomitant spectrophotometric alteration can be used to quantitate the amount of biotinylated-analyte conjugate which is present.

FIG. 5 depicts the colorimetric assay for (biotin)$_2$-digoxin displacing NABA from a NABA-avidin complex. Specifically, various concentrations of (biotin)$_2$-digoxin from 0, 0.5, 1.0. 2.0 E-9 moles were added to one ml of 5 E-10 moles avidin/20 E-10 moles NABA-avidin complex. Absorbance was measured at 514 nm on an HP 8452 A spectrophotometer.

3b) Fluorescence quenching

Burnstein et al. (Photochem. Photobiol (1973), 18: 263–279) reported that the binding of biotin to avidin alters the fluorescence emission spectrum of avidin. The maximum emission wavelength and quantum yield of the biotin-avidin complex changes when compared with native avidins. Kurzban et al. (Biochemistry 1989, 28: 8537–8542) found the binding of biotin to avidin changes the environment of tryptophan residues and reduces the fluorescence bandwidth and quenches the fluorescence 20–29% of the initial avidin fluorescence.

It has been found that an azo dye, such as NABA, dramatically quenches the fluorescence emission of avidin. The number of binding sites in avidin or streptavidin occupied by NABA is inversely proportional to the intensity of fluorescence emission of avidin. The maximum fluorescence quenching of avidin by the NABA is 83–85% and 50–56% of streptavidin respectively. The results can be seen in FIGS. 6 and 7. The azo dye, NABA can be rapidly replaced from the avidin binding sites by a free biotin or a biotin conjugate.

Figure 6:
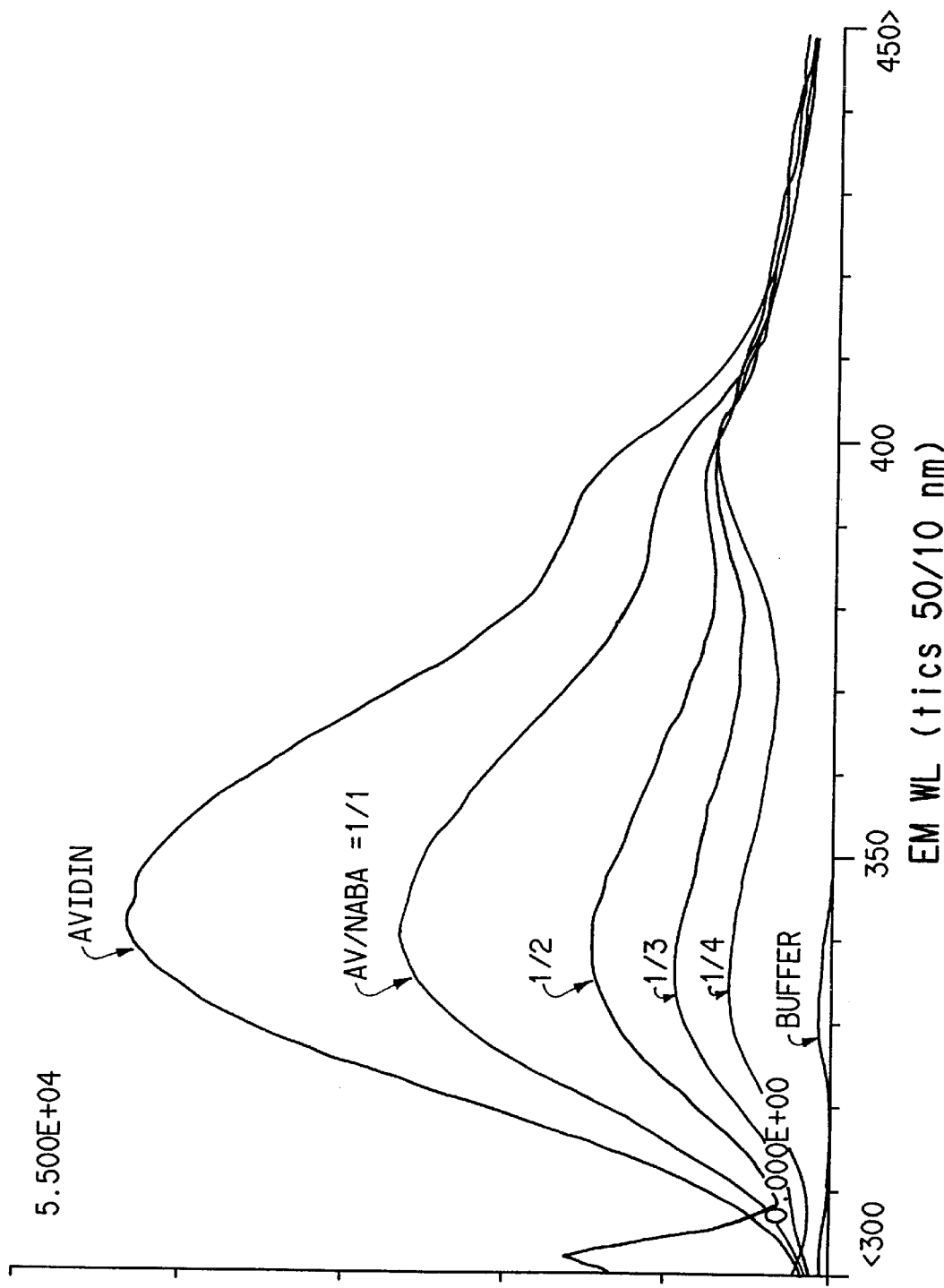
FIG. 6 depicts the fluorescence quenching of avidin by NABA.

In FIG. 6, scans of various amounts of NABA at molar ratios of avidin: NABA of 1/1, 1/2, 1/3, 1/4 showed quenching of 5 E-10 moles/ml of avidin fluorescence emission as measured on an AMINCO Photon Counter 8000C. The parameters were as follows: excitation wavelength was at 300 nm, emission wavelength was at 340 nm, scanning from 300 to 450 nm; EX/EM resolution band width: 16/8 nm; signal integration time: one second.

Figure 7:
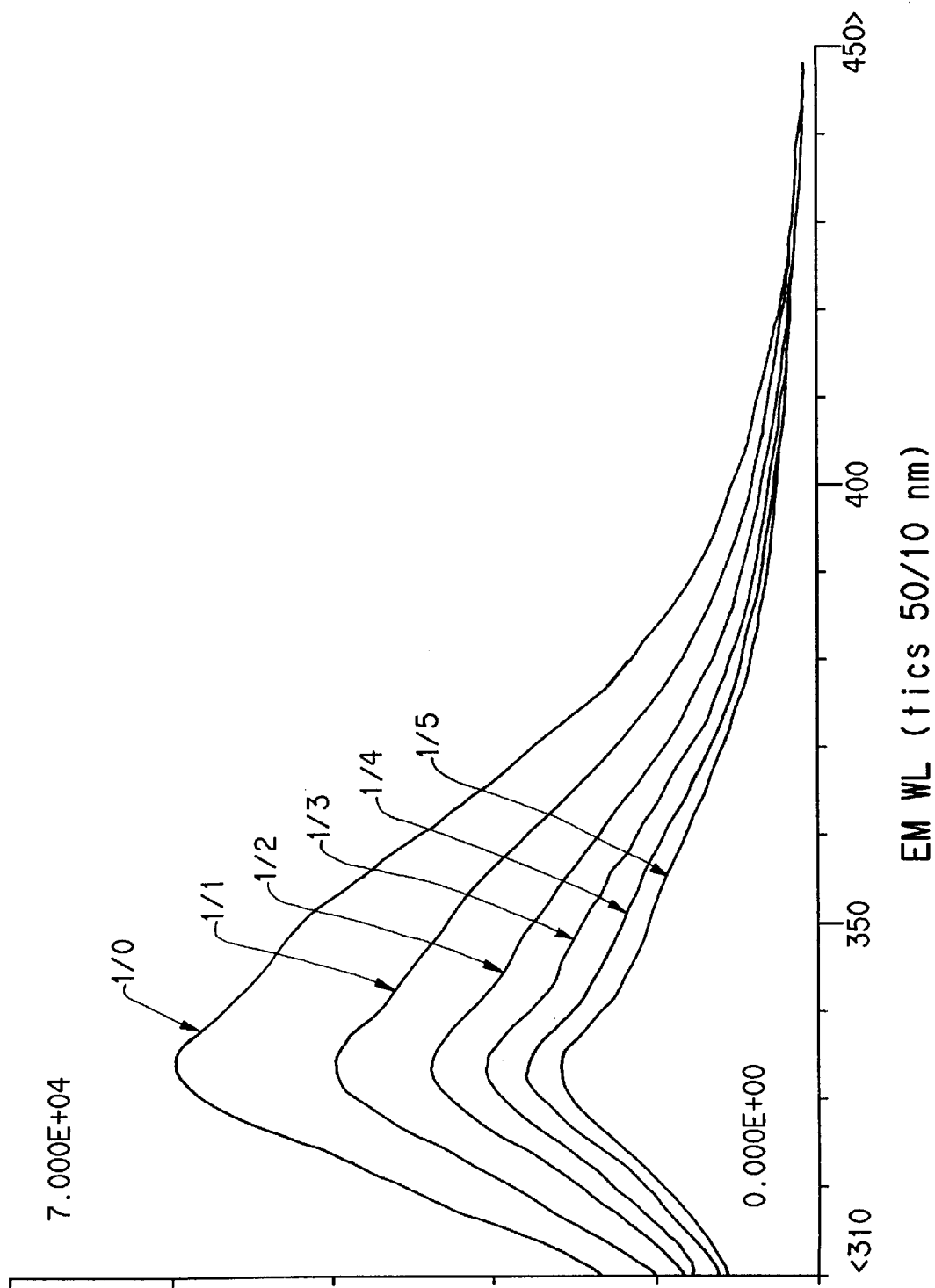
FIG. 7 depicts the fluorescence quenching of streptavidin by NABA.

FIG. 7 depicts scans of various amounts of NABA at molar ratio of AV/NABA of 1/1, 1/2, 1/3, 1/4 and 1/5 quenching 5 E-10 moles/ml of streptavidin fluorescence emission of an AMINCO Photon Counter 8000C. The parameters were as follows: excitation wavelength was at 300 nm, emission wavelength was at 340 nm, scanning from 300 to 450 nm; EX/EM resolution band width: 8/8 nm; signal integration time: one second.

3b.I) Fluorescence quenching assay

Figure 8:
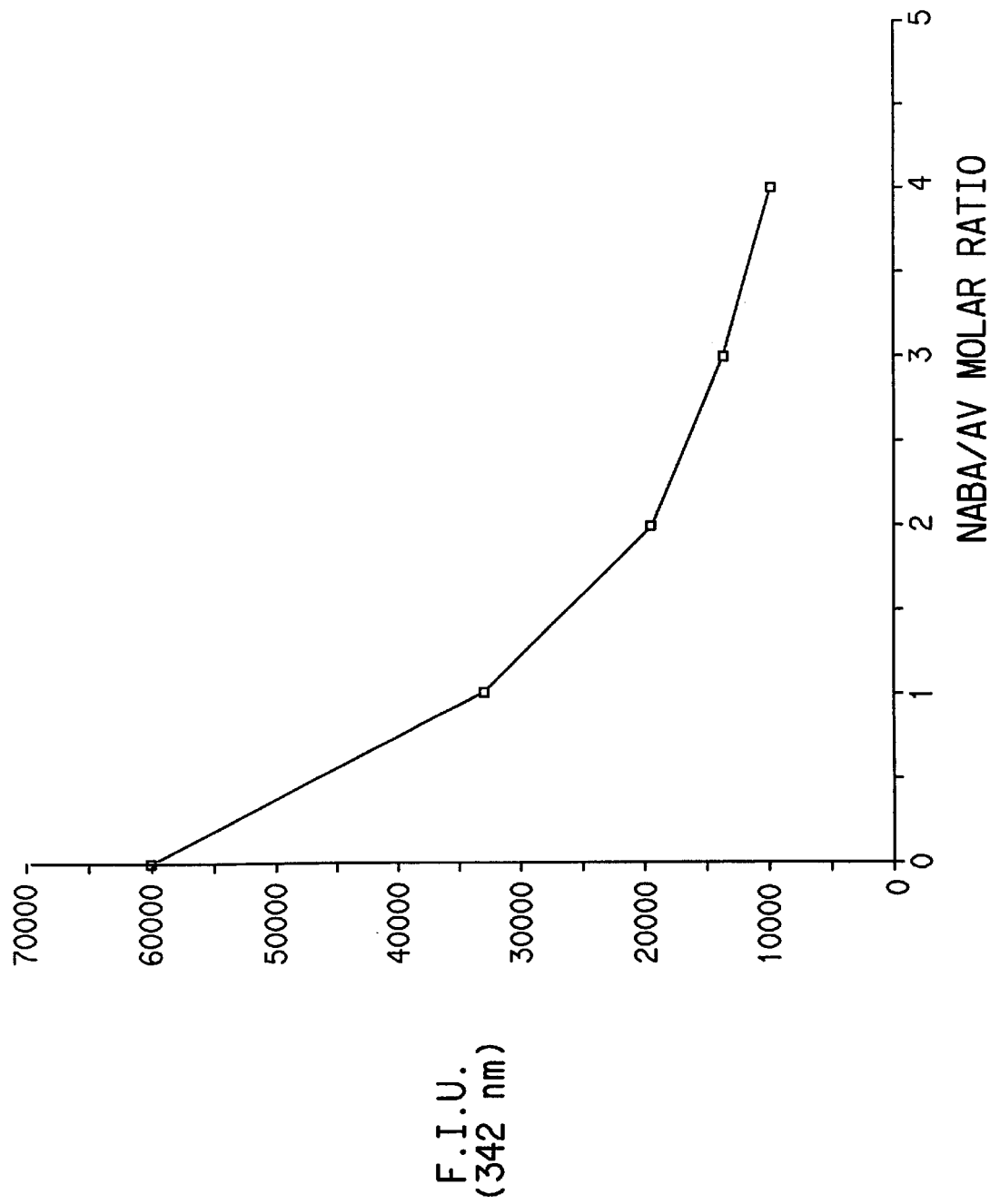
FIG. 8 depicts a fluorescence quenching assay using various amounts of NABA and a fixed amount of avidin.

Avidin or streptavidin (5 E-10 moles in 1 ml of 0.1 M sodium bicarbonate, pH 8.5) was pipetted into a fluorescence cuvette and excited at 300 nm. The. fluorescence emission spectrum was recorded on a spectrofluorometer (8000C Photon Counter, SLM Instruments, Inc., Urbana, Ill.). NABA stock solution of $5 \times 10^{-11}$ mole/ml was prepared in sodium biocarbonate buffer pH 8.5. Aliquot of 10 µl NABA solution was added to avidin or streptavidin solution. The fluorescence signal was again measured. The process was repeated 4 times sequentially. Corrections were made for buffer fluorescence, the inner filter effect, and dilutions. The spectra were taken at each concentration of quencher, NABA, in the presence of avidin or streptavidin. The standard curve of NABA to avidin ratio can be constructed against the relative fluorescence emission intensity unit at 342 nm of avidin. Results were measured on an AMINCO Photon Counter 8000C (FIG. 8).

3b.II) Fluorescence Recovery Assay (estimate biotin)

Figure 9:
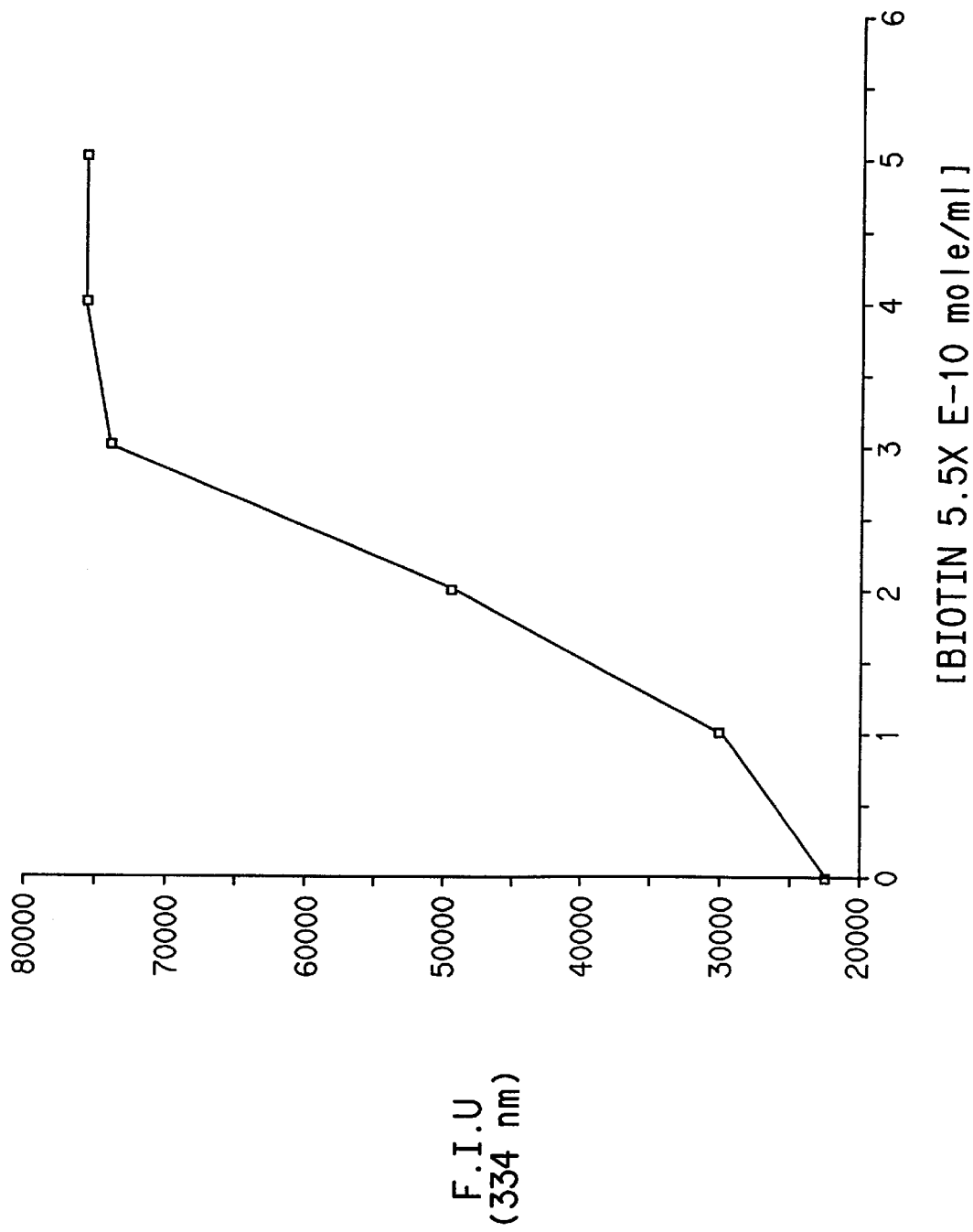
FIG. 9 depicts a fluorescence recovery assay using various amounts of biotin to displace NABA from a fixed amount of avidin-NABA complex.

1 ml of avidin-NABA complex solution ($5 \times 10^{-10}/20 \times 10^{-10}$ mole/ml of AV/NABA, in 0.1 M sodium bicarbonate buffer at pH 8.5) was pipetted into a 1-cm fluorescence cuvette. The fluorescence spectrum of the complex was measured in a spectrofluorometer. Biotin (Sigma Chemical Co.) 10 µl of $5 \times 10^{-11}$ mole/ml was added to the avidin-NABA complex solution and the fluorescence spectrum was recorded on an AMINCO Photon Counter 8000C. This process was repeated 4 times. The ratio of biotin to avidin was plotted against the fluorescence emission intensity unit at 342 nm of the avidin-NABA complex. The same assay can be used to determine the amount of biotinylated analyte present in the sample. (Biotin)$_2$-digoxin can displace NABA from the avidin-NABA complex and the concomitant spectrophotometric change can be used to determine the amount of biotinylated analyte present in the sample as shown in FIG. 9.

3c) Fluorescence polarization

Schray et al. (Anal. Chem. 1988, 60: 853–855) used a fluorescein-biotin conjugate in a fluorescence polarization study to quantitate biotin or avidin. The rapid molecular tumbling, fluorescence radiation from small molecules is depolarized when excited by polarized light. Complexation by a high molecular weight molecule slows tumbling of the resultant complex and allows the emitted radiation to remain partially or totally polarized. Thus, complexed biotin-fluorescein-avidin and the uncomplexed biotin-fluorecein fluorescent molecules may be distinguished by the polarization of the emitted light.

It is believed that when the fluorescent molecule, NABA, binds to avidin in a biotin-binding site, it totally blocks the 4 tryptophan residues in the binding site from tumbling or rotating. The resultant NABA-avidin or streptavidin complex thus allows the emitted radiation light to polarize.

3c.I) Polarization assay

Avidin ($3.65 \times 10^{-10}$ mole in 1 ml of 0.1 M sodium bicarbonate buffer, pH 8.5 was added to a quartz cuvette. The avidin polarization was measured in a SLM spectrofluorometer 8000C Photon counter with polarizer installed. NABA stock solution was $4 \times 10^{-11}$ mole/ml in sodium bicarbonate buffer pH 8.5. After avidin or streptavidin's polarization value was measured, 9 µl aliquots of NABA were added, and the polarization values were again measured. Corrections were made for buffer fluorescence, and the dilutions. The amount of NABA was added to avidin to yield a 4/1, 3/1, 2/1 and 1/1 molar ratio of NABA to avidin in the final mixture. Each complex polarization value was calculated based on the following equation:

$$\text{Polarization} = \frac{(Ivv - Ivh) \times G}{(Ivv + Ivh) \times G}$$

Ivv represents fluorescence intensity with vertical exciting light and measuring with vertical emission light. Ivh represents fluorescence intensity with vertical exciting light and measuring with horizontal emission light. G is the correction factor for the instrument and is determined by G=Ihv/Ihh. Ihv represents fluorescence intensity with horizontal exciting light and measuring with vertical emission light. Ihh represents fluorescence intensity with horizontal exciting lgiht and measuring with horizontal emission light.

Figure 10:
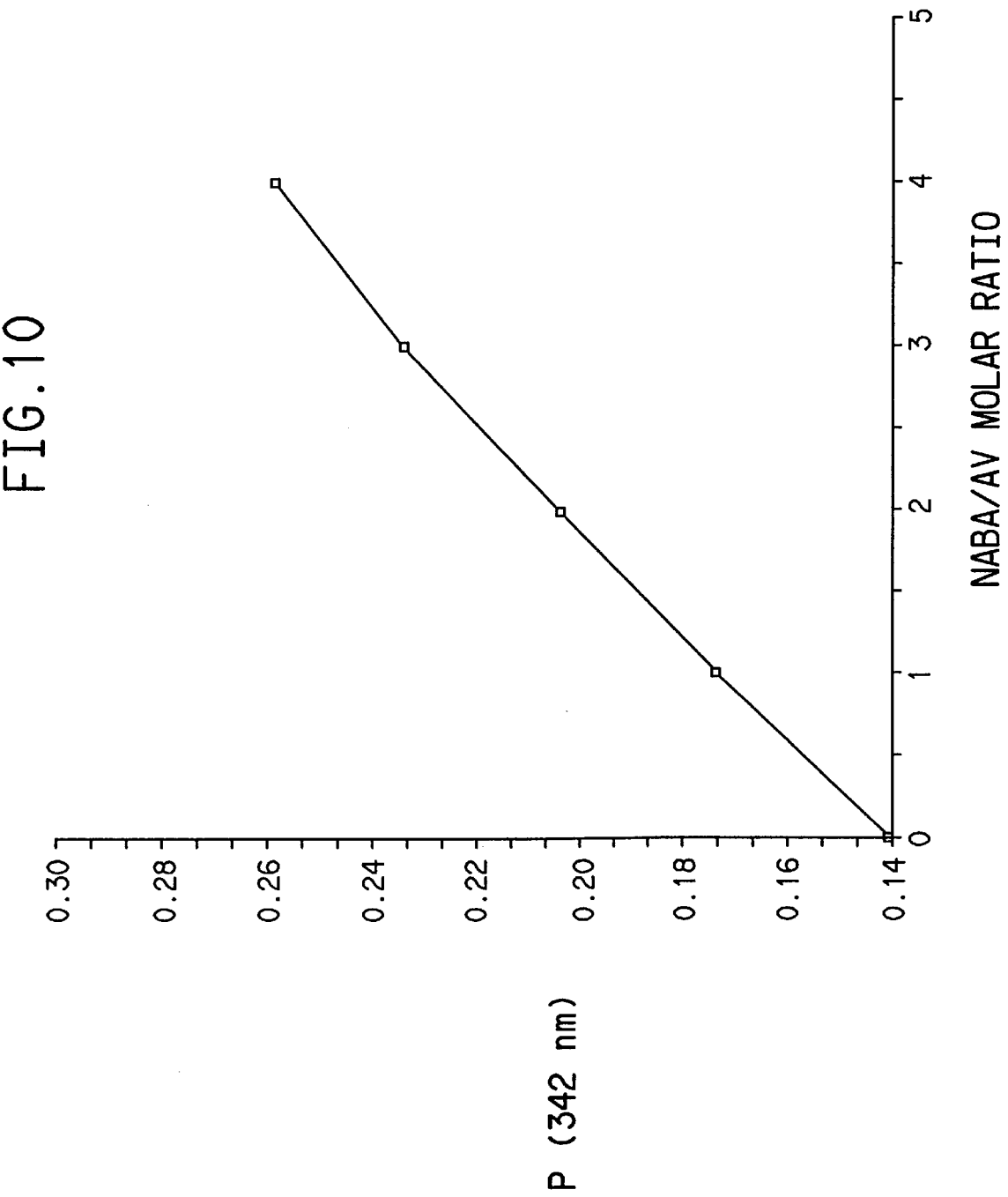
FIG. 10 depicts a fluorescence polarization assay using various amounts of NABA at molar ratios of NABA/avidin—4/1, 3/1, 2/1, 1/1, and 0/1.

The standard curve can then be constructed for use in determining an unknown (See FIG. 10).

3c.II) Depolarization (Biotin Assay)

1 ml of avidin-NABA complex solution (3.65 E-10/14.6 E-10 mole/ml of AV/NABA, in 0.1 M sodium bicarbonate buffer at pH 8.5) is pipetted into a 1-cm fluorescence cuvette. The complex fluorescence polarization value is measured in a fluorometer. The sample of various concentrations of biotin is added to avidin-NABA complex in the above buffer. The mixtures are incubated at room temperature for 2 minutes and then each combination polarization value is determined. The concentrations of biotin against the fluorescence polarization value of the avidin-NABA complex can be constructed to determine the unknowns.

C. Homogeneous Immunoassay 1 ml of NABA-avidin complex solution (10 ml of avidin solution 5 E-10 mole/ml in bicarbonate buffer was mixed with 200 E-10 mole in 100 ml of NABA to form the NABA-avidin complex stock solution) was pipetted into a fluorescence cuvette and the fluorescence emission of the complex was measured in a fluorometer (Aminco Photon counter 8000C).

Fresh digoxin (Simga Chemical Co.) solution at 4 E-9 mole/ml in DMSO solution was prepared and then a series dilution of 1/100 were made into sodium bicarbonate solution, pH 8.5. The free digoxin at various concentration (0, 2 E-10, 4 E-10, and 6 E-10 and 8 E-10 moles) were preincubated with 6 E-10 mole of (biotin)$_2$-digoxin and 3 E-10 moles of polyclonal rabbit anti-digoxin IgG for 20 minutes at 37° C. After a period of 20 minutes, then (5 E-10moles/20E-10 moles) of avidin/NABA complex was added to each level of free digoxin. The fluorescence emission of each reaction mixture was then measured in a fluorometer. The control set included free avidin, avidin-NABA complex, free anti-digoxin-IgG, and (biotin)$_2$-digoxin/anti-digoxin-IgG complex. Corrections for the buffer, inner filters, and the dilutions were made. The standard curve of free digoxin against fluorescence intensity unit was constructed. This standard curve is depicted in FIG. 11.

What is claimed is:

1. A homogeneous assay to determine the presence of absence of an analyte which is a first member of a specific binding pair in a sample which comprises:
   a) reacting biotinylated analyte, sample suspected to contain free analyte and a constant amount of a second member of the specific binding pair;
   b) reacting all of the products of step (a) with a constant amount of a complex comprising avidin and a fluorescence-quenching 2-[4(hydroxy-1-naphthalenyl)azo]benzoic acid (NABA) compound, said NABA compound binding to the biotin-binding site of avidin with a binding constant less than $10^{15}$ $M^{-1}$;
   c) measuring a quantifiable change in quenching of the fluorescence of tryptophan residues in at least one biotin-binding site of avidin or a quantifiable change in polarization of the fluorescence of tryptophan residues in at least one biotin-binding sit of avidin; and
   d) correlating said quantifiable change with the amount of free analyte in the sample.

2. A homogeneous assay to determine the presence or absence of an analyte which is a first member of a specific binding pair in a sample which comprises:
   a) reacting sample suspected to contain free analyte, an analyte-2-[4(hydroxy-1-naphthalenyl)azo]benzoic acid (NABA) conjugate and a constant amount of a second member of the specific binding pair wherein the conjugate binds to the biotin-binding site of avidin with a binding constant less than $10^{15}$ $M^{-1}$ through the NABA compound, said conjugate having the structure:

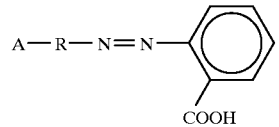

wherein
   A is the analyte; and
   R is a naphthalenyl moiety;
   b) reacting all of the products of step (a) with a constant amount of avidin;
   c) measuring signal produced; and
   d) correlating the measurement obtained in step (c) with the amount of free analyte in the sample.

3. An assay according to claim 2 wherein the signal measured is (i) a quantifiable change in absorbance of bound NABA azo compound in the visible region of the spectrum, (ii) a quantifiable change in quenching of the fluorescence of tryptophan residues in at least one biotin-binding site of avidin, and/or (iii) a quantifiable change in polarization of fluorescence of tryptophan residues in at least one biotin-binding site of avidin.

* * * * *